United States Patent [19]
Willoughby

[11] Patent Number: 5,285,064
[45] Date of Patent: Feb. 8, 1994

[54] METHOD AND APPARATUS FOR INTRODUCTION OF LIQUID EFFLUENT INTO MASS SPECTROMETER AND OTHER GAS-PHASE OR PARTICLE DETECTORS

[75] Inventor: Ross C. Willoughby, Pittsburgh, Pa.

[73] Assignee: Extrel Corporation, Pittsburgh, Pa.

[21] Appl. No.: 40,073

[22] Filed: Mar. 30, 1993

Related U.S. Application Data

[63] Continuation of Ser. No. 831,665, Feb. 6, 1992, abandoned, which is a continuation of Ser. No. 573,868, Aug. 28, 1990, abandoned, which is a continuation of Ser. No. 393,846, Aug. 14, 1989, Pat. No. 4,968,885, which is a continuation of Ser. No. 22,725, Mar. 6, 1987, abandoned.

[51] Int. Cl.[5] .............................................. H01J 49/04
[52] U.S. Cl. ..................... 250/288; 250/283; 73/863.11; 73/863.12; 73/864.81
[58] Field of Search .................... 250/288 A, 288, 283; 73/863.11, 863.12, 864.81

[56] References Cited

U.S. PATENT DOCUMENTS

| | | | |
|---|---|---|---|
| 3,997,298 | 12/1976 | McLafferty et al. | 250/288 A |
| 4,298,795 | 11/1981 | Takeuchi et al. | 250/288 A |
| 4,358,302 | 11/1982 | Dahneke | 250/288 |

Primary Examiner—Jack I. Berman
Attorney, Agent, or Firm—Penrose Lucas Albright

[57] ABSTRACT

Methods and apparatus for liquid sample introduction into chemical detectors that require the sample to be transformed from a flowing stream into either gaseous or particulate states. The effluent from either a process stream or a liquid chromatograph is nebulized by combined thermal and pneumatic processes within an inner fused silicon capillary tube heated by conduction from a surrounding electrical resistance heated outer capillary tube composed of a pure metal having a comparatively high linear relationship between temperature and electrical resistance to provide a uniform conduction of heat energy to the inner tube to form a well-collimated, partially or completely desolvated aerosol, with the less volatile solute components of the sample stream remaining in the particulate state. The gaseous components of the aerosol are separated from the solvent-depleted solute particles using either cryotrapping or momentum separation. The enriched solute particles are vaporized, ionized, and/or detected by suitable gas-phase or particle detectors. The device is primarily an interface between the liquid chromatograph or process streams and the mass spectrometer.

8 Claims, 6 Drawing Sheets

METHOD AND APPARATUS FOR INTRODUCTION OF LIQUID EFFLUENT INTO MASS SPECTROMETER AND OTHER GAS-PHASE OR PARTICLE DETECTORS

This is a continuation of U.S. application Ser. No. 07/831,665, filed Feb. 6, 1992, now abandoned, which is a continuation of U.S. application Ser. No. 07/573,868, filed Aug. 28, 1990, now abandoned, which is a continuation of U.S. application Ser. No. 07/393,846, filed Aug. 14, 1989, (now U.S. Pat. No. 4,968,885, issued Nov. 6, 1990), which is a continuation of U.S. application Ser. No. 07/022,725, filed Mar. 6, 1987, now abandoned.

BACKGROUND OF THE INVENTION

Successful liquid sample introduction into gas-phase or particle detectors is dependent upon the interface between the liquid stream and the detector. The coexistence of continuous liquid sample introduction and normal operating requirements of the gas-phase detectors present compatability problems. Difficulties are sometimes encountered in accommodating the mass flow from the liquid stream into the detector. In addition, degradation of thermally labile sample components may occur during the evaporation processes prior to gas-phase detection. In the case of gas-phasedetectors such as mass spectrometers, where detection occurs at a reduced pressures, vacuum locks and pumping requirements may be considerations. General requirements for interfaces between liquid streams and gas-phase detectors are: (1) The sample must be evaporated prior to detection; (2) Minimal thermal degradation should occur during the sample evaporation process; (3) The sample transport efficiency should be sufficiently high so that adequate sensitivity is observed; (4) The normal operating conditions of the detector should be maintained during sample introduction; and (5) The sample's composition should be maintained while being transported to and through the interface (e.g. minimal chromatographic band broadening). Success in interfacing liquid streams to gas-phase detectors depends on how well the foregoing requirements are met.

The principal application of the present device to gas-phase detection of liquid streams is the introduction of the effluent from a liquid chromatograph into a mass spectrometer. The interfacing between liquid chromatography (LC) and mass spectrometry (MS) is referred to as LC-MS. Although the present invention relates to the general field of liquid sample introduction into gas-phase or particle detectors, most prior work in this area has concentrated on LC-MS because it has presented formidable obstacles to interface design. This background discussion therefore focuses on LC-MS.

Complex gas-phase detectors, mass spectrometers, detect gas-phase ions formed by a variety of mechanisms; electron impact (EI) ionization and chemical ionization (CI) are the most commonly practiced approaches. With EI ionization, the sample gas at $10^{-3}$ – $10^{-6}$ torr is bombarded with electrons of sufficient energy (generally 70 eV) to excite electronic energy levels of sample molecules beyond the ionization potential so that an electron is removed from the sample molecule, making it a positive ion. Upon sample ion formation in the EI mode, excess energy imparted to the sample molecule from the bombarding electron causes bond cleavage or fragmentation. It is a characteristic and reproducible nature of EI fragmentation, indicative of molecular structure, that provides this technique with broad utility for the analysis of samples with an unknown composition. In contrast, the CI mode operates at higher pressures relative to EI (typically at one torr), whereby the ionization occurs due to collision of sample molecules with reagent gas ions. The analytical utility of CI is generally found in the presence of molecular weight information. With CI, the limited and irreproducible fragmentation of sample molecules is essentially of no value. It should be stressed that the ionization process ultimately determines the qualitative information obtained with the mass spectrometer. Alternative ionization techniques are atmospheric pressure ionization (API) at 760 torr and field ionization at $10^{-4}$ torr. It is preferable to use a variety of ionization techniques, including EI and CI, to obtain the maximum information for a given sample. LC-MS techniques that place a restriction upon ionization conditions also are limited in the sample information obtained for a given analysis.

Mass spectra of many compounds, usually those ionized under EI conditions, have been compiled in massive computerized data-base libraries for subsequent comparison with acquired spectra (fragment ions) from samples of unknown composition. It would be therefore a significant advantage for LC-MS devices to make use of such spectral libraries because computer comparisons can be made in a matter of seconds. Hence, for the wide use there is a need for LC-MS devices that utilize EI ionization modes. Unfortunately, only few prior art devices are reported to have the capability of producing EI spectra of thermally labile and/or involatile compounds.

Effluent from either a liquid chromatograph or a liquid process stream must be accommodated by the mass spectrometer interfacing techniques. The pressure requirements for ionization, as discussed, are dependent upon the mode of ionization, and limited by the mass flow into the ionization region of the mass spectrometer and the pumping capacity of the mass spectrometer. The evaporation of liquid flowing at 1-2 mL/min may produce as much as a liter per minute of gaseous sample at STP (Standard Temperature and Pressure), which amounts to $10^8$ liters per minute of gas at $10^{-5}$ torr (i.e. EI conditions), far exceeding the pumping capabilities of conventional mass spectrometers. Ionization techniques which occur at pressures of one millitorr or higher, such as CI, require less pumping but usually result in significant ion-molecule reaction chemistry which yields little structural fragmentation information. Due to the requirement of low pressure for EI ionization, direct introduction of a continuous stream of liquid from a liquid chromatograph is difficult to attain without extremely large capacity pumping systems such as cryogenic pumping.

The evaporation or desorption process, whereby the sample is transformed into gas, may also result in thermal degradation (pyrolysis), reactions, or rearrangements of the original sample molecules. These sample losses are most prevalent with sample components that are thermally labile and/or involatile, commonly separated by liquid chromatography. Mass analysis of these thermally labile and/or involatile molecules is usually limited by the inability to produce intact gas-phase ions of these species. Therefore, it is important in development of interfaces between the LC and MS to vaporize the sample with minimal degradation or loss of analyte.

There have been a variety of approaches to interfacing the LC with the MS and this work as been extensively reviewed. (1,2,3,4). The common objective of all interfacing techniques is efficiency in the production of gas-phase sample ions.

Direct Liquid Introduction (DLI) is one of the simplest approaches to interfacing LC with MS. With DLI, the effluent from a liquid chromatograph flows through a tiny circular aperture or tube with a diameter on the order of three to ten micrometers. A high velocity cylindrical liquid jet is directed into the ionization chamber. There have been a wide variety of designs using this approach and they all have the same basic configuration (reviewed in 5 and 6). The jet may proceed through a heated desolvation region before entering the ionization region to aid in solvent evaporation. This technique typically had been limited to micro-bore LC flow rates, less than one hundred microliters per minute. To accommodate direct introduction of liquid into ion source, cryogenic pumping has been used to trap the excess sample onto a cold surface of the outside of the ion source. In cases where normal LC flow rates are used, 1-2 mL/min, the effluent has been split, leaving only a fraction of the sample to be sampled into the mass spectrometer. Another limitation of the DLI technique is that the spectra produced yield only CI data. Little or no structural information is thus obtained, in contrast to EI. In addition, more costly differential pumping is required to maintain the mass analyzer pressures sufficiently low. In practice DLI has been plagued by repeated clogging of the micron sized orifices, causing the approach to be cumbersome, with significant downtime. The alignment and the instability of micron sized liquid jets also make DLI experimentally difficult in that data acquired may be noisy and irreproducible. However, the advantage of this technique is the lack of thermal degradation when analyzing thermally labile compounds. Further discussion of this technique may be found in U.S. Pat. Nos. 3,997,298 of Dec. 14, 1976 and 4,403,147 of Sep. 6, 1983.

Mechanical Transport (MT) is an LC-MS approach whereby the effluent from the LC is deposited on a moving surface, such as a wire or belt. Heat may be applied to the sample to remove solvent and the desolvated sample is mechanically transported on the wire or belt through a series of vacuum locks into the low pressure ion source of the mass spectrometer. Both EI and CI mass spectra have been obtained with this technique. A limitation of this technique is the requirement that the sample be evaporated or desorbed from the moving surface prior to ionization. Thermal degradation may occur during the thermal evaporation process. Operation of mechanical transport devices is frequently cumbersome due to design complexity and jamming of moving parts. The chromatographic profile of sample may be degraded by the non-uniform application of sample upon the moving surface. This approach is explained in greater depth in U.S. Pat. No. 4,055,987 of Nov. 1, 1977.

Thermospray (TSY) is a more widely used approach to LC-MS. The effluent from the LC flows through a thermal vaporizer into a heated vaporizer chamber in the ion source region of the MS. The thermal vaporizer transforms the sample into an ion-vapor plasma in a vaporizer chamber. A small fraction of the ion-vapor is sampled into the ion optics region of the mass spectrometer through a small aperture. The efficiency of sampling analyte through the sampling aperture is quite low. The majority of the ion-vapor is evacuated through a roughing line connected to the vaporizer chamber. As with DLI, costly differential pumping between the ion optics region and the mass analyzer region is required to maintain an adequate vacuum. The vaporization process produces gas-phase reagent ions when buffered solutions, such as aqueous ammonium acetate, are pumped through the thermal vaporizer. This ionization process, known as thermospray ionization, produces CI-like spectra. Under normal operation conditions, thermal degradation has been observed with the use of the thermal vaporizer; however, a large number of thermally labile compounds have been analyzed with this technique with minimal degradation. TSY has several limitations, most notably is the lack of structural information such as that obtained under EI ionization conditions. The response of various compounds depends upon the chemical nature of the substance being analysed. Consequently, it is sometimes difficult to predict response for poorly characterized samples. Thermospray processes are described in further detail in Canadian Patent 1,162,331 of Feb. 14, 1984, and U.S. application Ser. No. 527,751, filed Aug. 30, 1985, and a continuation thereof filed Ser. No. 832,743, issued as U.S. Pat. No. 4,730,111, to M. Vestal and C. Blakley on Mar. 8, 1988.

Monodispersed Aerosol Generation Interface for Combining liquid chromatography with mass spectrometry (MAGIC) is an approach to LC-MS whereby effluent is pumped through a tiny orifice or tube, forming a stable liquid jet. The liquid jet breaks up into uniformly sized or monodispersed droplets. The droplets are dispersed in a near-atmospheric pressure desolvation chamber with a dispersion gas that serves to prevent coagulation of the droplets as well as conduct thermal energy to the droplets a resulting in rapid desolvation. This approach requires a large diameter desolvation chamber at near atmospheric pressure to allow efficient desolvation. The effect of lowering desolvation chamber pressure on the rate of solvent evaporation has theoretically been treated by Fuchs and Sutugen (16). The rate of evaporation of a liquid droplet is significantly reduced with decreases in pressure. In the absence of dispersion gas, the droplets receive insufficient thermal energy which prevents their complete desolvation. Dispersion gas flows of greater than one liter per minute have been used in order to maintain sufficiently high pressure in the desolvation chamber. Subsequent to desolvation, solvent-depleted solute particles are accelerated through a nozzle into a vacuum chamber to form a high velocity aerosol beam. The lighter solvent vapor and dispersion gas, compared to the more massive solute particles, expand outward from the axis of the aerosol beam, leaving a collimated particle beam devoid of gaseous components. The gaseous components of the aerosol beam are removed in a two-stage pressure reduction process, accomplished by directing the particle beam through two successive skimmers that separate two successively lower pressure vacuum chambers. The solute particle beam proceeds through the skimmers into the ion source region where enriched solute is thermally desorbed from surfaces in the ion source region and ionized by conventional CI or EI ionization process.

The magic approach to LC-MS has the advantage of ionizing solute under EI conditions. However, the requirement of near atmospheric pressure desolvation significantly reduces the solute transport efficiency into the low pressure ion source of the mass spectrometer.

The addition of high flow rates of dispersion gas creates turbulence at the nozzles and significant loss in transport efficiency is observed due to impact on the surfaces of the skimmers and nozzles as well as walls of the desolvation chamber. The requisite high gas lead also tends to increase the solid angle expansion of the particle beam and to favor the use of a less efficient two-stage separator device. Because of these conditions, transport efficiency of solute into the ion source is generally on the order of five percent. With MAGIC, the mobile phase composition does not affect the response for various analytes as does the thermospray technique which in some cases requires mobile phase additives for sensitive response. Also, no differential pumping is required with this technique when EI ionization is the only mode employed. Additional details on this technique are presented in U.S. patent application Ser. No. 623,711 filed Jun. 22, 1984, by R. Browner and R. Willoughby, which issued Dec. 16, 1986 as U.S. Pat. No. 4,629,478, and in a continuation-in-part thereof, U.S. patent application Ser. No. 841,314, which issued Aug. 9, 1988, as U.S. Pat. No. 4,762,995.

MAGIC can be considered a particle beam introduction technique. For this discussion, particle beam introduction is considered as a technique of accelerating an aerosol through a nozzle into successive vacuum chambers while skimming the aerosol particles on axis, forming a particle beam, and pumping away gaseous components of the aerosol beam off-axis. The result of this process is the efficient separation of aerosol particles from gaseous material, with the particles being transported more efficiently into lower pressure regions because of the higher momentum of the particle when compared to the gas molecules. Prior particle beam introduction techniques for mass spectrometry have applied to two areas: (1) Real-time aerosol monitoring (7-9); and (2) Liquid sample introduction where an aerosol generation step precedes the particle beam introduction (10-14). The MAGIC technique is an example of the latter. The present invention also includes a particle beam solute enrichment step when applied to sample introduction into the mass spectrometer.

Performance of particle beam introduction techniques is dependent upon the properties of the aerosol. The solid angle dispersion of the particle beam is dependent upon the size of the solute particles, the pressure from the aerosol source, and the geometry of the nozzle. Israel and Friedlander (15) experimentally showed the relationships of these parameters on particle beam dispersion. Their results show: (1) Particle beam angular dispersion increases with aerosol source pressure; (2) Particle beam angular dispersion decreases with increase in particle size; and (3) Particle beam expansion is more uniform with changes in particle size when capillary versus converging nozzles are used. Therefore, the nature of the aerosol generation process in terms of gas flow and pressure, and particle size and distribution ultimately determines the efficiency of the particle beam introduction technique.

A variety of aerosol generators have been used with the particle beam approach to liquid sample introduction into the mass spectrometer. These include the Berglund-Liu monodisperse aerosol generator (8,10-14), the Willoughby-Browner monodisperse aerosol generator (14), and DeVilbiss and ultrasonic nebulizer (10-13). A major limitation of prior particle beam techniques was the difficulty in desolvation of the aerosol droplets subsequent to aerosol generation. Prior techniques required a desolvation chamber or increases gas load to remove solvent from the droplets. The generation of droplets greater than about ten microns in diameter with prior aerosol generation techniques leads to greater likelihood of particle losses in the desolvation chambers and nozzles due to impaction or settling process. The aerosol generation process of the present invention is designed to permit precise control over aerosol properties, including the droplet size, direction, and rate of evaporation. With enhanced control over the aerosol generation and desolvation processes, the efficiency of the particle transport to various detectors is increased.

The solid angle dispersion of particle beams has been shown to in aerosol source pressure (15). Thus, the prior particle beam techniques that require high gas loads for aerosol generation or desolvation tend to have more divergent particle beams. This requires that only part of the particle beam cross-section can be sampled through axial skimmers because pressures in subsequent chambers exceed the upper pressure limitation of the detector. Thus, the entire cross-section of a less divergent particle beam could in theory be collected with the same skimmer diameter while maintaining the same detector pressure. The result of a less divergent particle beam is more efficient sample transport to the detector. Consequently, an objective of the present device is to decrease the gas load from the aerosol generation process to enhance sample transport efficiency.

The use of particle beam techniques for sample introduction into the mass spectrometer has demonstrated the ability to produce spectra under electron impact ionization conditions (7-14). A major objective of the present device is to enhance the ability to volatilize the particles once the particle beam enters the ion source region of the mass spectrometer. The objective is to form intact gas-phase molecular species of substances originating in the particle. But prior particle beam sample introduction devices have experienced difficulty in forming intact molecular ions due to thermal fragmentation of molecules during evaporation from heated surfaces (8). Particle volatilization process depends upon the equilibrium surface vapor pressure of molecules originating from the particles, the temperature and material of the particle beam collection surface, and the presence of other components in the particle matrix. Control of these factors is essential to the performance of the present device.

Other applications of liquid sample introduction into gas-phase or particle detectors have been reported for light scattering (17), flame ionization (18), atomic absorption or emission spectrophotometry (19). The enhanced control of aerosol generation, desolvation and solute enrichment with the present device is applicable to a variety of detectors.

Sources for the above mentioned in the above background history are:

1. P. J. Arpino, J. Chormatogr. 323, 3 (1985).
2. D. E. Games, Adv. Chomatogr. 21, 1 (1983).
3. C. G. Edmonds, J. A. McCloskey, V. A. Edmonds, Biomed Mass Spectrom. 10, 237 (1983).
4. R. C. Willoughby, R. F. Browner, Trace Analysis. Vol. 2, p. 69, ed. J. F. Lawrence. Academic Press (1982).
5. W. M. A. Niessen, Chromatographia, 21, 5 (1986).
6. W. M. A. Niessen, Chromatographia. 21, 5 (1986).
7. J. J. Stoffels. "A direct Air-Sampling Inlet for Surface Ionization Mass Spectrometry of Airborne Particles," presented at the 24th Annual Meeting of ASMS, San Diego, Calif. 1976.
8. M. P. Sinha, C. E. Griffin, D. D. Norris, and S. K. Friedlander, "Analysis of Aerosol Particles by Mass Spectrometry," presented at the 28th Annual Meeting of ASMS, New York, N.Y. 1980.
9. J. Allen and R. K. Gould, Rev. Sci. Instum. 52 (6), June 1981.
10. F. T. Greene, "Particulate Impact Mass Spectrometry," presented at the 23rd Annual Meeting of ASMS, Houston Tex., 1975.
11. F. T. Greene, "Mass Spectrometry of Nonvolatile Materials and Solutions y the Particulate Impact Technique," presented at the 24th Annual Meeting of the ASMS, San Diego, Calif. 1976.
12. F. T. Greene, "Further Development of Particulate Impact Mass Spectrometry," presented at the 29th Annual Meeting of the ASMS, New York, N.Y. 1980.
13. F. T. Greene, "The Current Status of Particulate Impact Mass Spectrometry," presented at the 29th Annual Meeting of the ASMS, Minneapolis, Minn. 1981.
14. R. C. Willoughby, "Studies with an Aerosol Generation Interface for Liquid Chromatography with Mass Spectrometry," PhD. Thesis, Georgia Institute of Technology, 1983.
15. G. W. Israel and S. K. Friedlander. J. Colloid Interf. Sci. 24, 330 (1967).
16. N. A. Fuchs and A. G. Sutugen. "Highly Dispersed Aerosols". Ann Arbor Science, Ann Arbor (1970).
17. J. W. Jorgenson, S. L. Smith, and M. Novotny, J. Chromatogr., 142, 233 (1977).
18. E. Haakti and T. Nikkari, Acta Chem. Scand. 17, 2565 (1963).
19. R. F. Browner and A. W. Boorn, Anal. Chem. 56/7, 787A (1984).

The above sources are incorporated by reference herein.

SUMMARY OF THE INVENTION

The disclosed invention is a method and apparatus for introducing into analyical devices liquid effluent from process streams, flow injection streams, or liquid chromatographs into gas-phase or particle detectors. It is applicable to liquid sample introduction into a variety of analyical devices including mass spectrometers, flame ionization detectors, light scattering detectors, and other apparatuses suitable for determining the nature of analytes in the gaseous or particulate states.

Basic processes occurring in the present device are aerosol generation and desolvation, solute enrichment, and detection of solute by a suitable gas-phase or particle detector.

Aerosol generation with the present invention is obtained by concentric flow of liquid (inner flow) and gas streams (outer flow). The gas is heated by direct contact with a heat source, generally a heated tube that sheathes the gas. The tube is heated by controlled resistive heating of the tube or direct contact of the tube with a cartridge heater. By precisely controlling the flow of gas through the outer tube, the flow of liquid through the inner tube, the dimensions of both tubes, and the power imput for the heat source, the aerosol properties are precisely determined. Heat is conducted across the gaseous medium and therefore the thermal conductivity of the gas is preferred to be high (e.g. hydrogen, helium).

The amount of heat supplied across the gaseous medium to the liquid determines the degree of desolvation or evaporation of solvent that occurs during the aerosol generation process. The gas supply serves two functions in aerosol generation. First, it conducts the heat necessary for desolvation. Second, it confines or sheathes the aerosol particles, preventing the particles from wide dispersion and impacting chamber walls with expansion within an expansion chamber that receives the solvent, the solute and the sheathing gas. The solvent is so received entirely or almost entirely in the gas phase while the solute is in particulate form. The present device requires no desolvation chamber because solvent evaporation takes place entirely inside the inner tube of the aerosol generator.

The controlled aerosol generation and desolvation with the present device effectively separates the solvent from the solute due to the solute being generally less volatile than the solvent. The solvent is thus in the gas-phase and the solute remains in the particulate state.

Once separate in phase, solute enrichment occurs by one of the two methods. The first method of solute enrichment separates the solvent from the solute in a particle beam or momentum separator, where the higher momentum solute particles are carried more efficiently into progressively lower pressure regions separated by skimmer apertures. The present device utilizes either single or dual-stage particle beam pressure reduction. The particle beam configuration in the present device transports most of solute to the low pressure detection region while removing more than ninety-nine percent of the solvent. The second method of solute enrichment, separates solvent from the solute because of mobility of particles compared to gases. The gaseous solvent components of the aerosol having higher mobility interact appreciably with cold surfaces and are trapped on the surfaces, cryotrapping. The solutes, in the particulate state, are carried in the gas flow by a poorly condensable carrier gas such as helium or hydrogen, leaving the solvent vapors behind. A combination of cryotrapping and particle beam solute enrichment is a third alternative.

Detection of enriched solute with the present device is accomplished by a variety of means. One embodiment of the present invention uses particle beam enrichment to direct solute particles into the ion source of the mass spectrometer. The particle beam is intersected by sources which may include primary ion beams, laser beams, discharge plasmas, electron beams, electric fields, or magnetic fields. Under these operating conditions, energy for solute evaporation and ionization is supplied directly to the solute particles during flight. Another embodiment utilizes a target surface to collect the solute particles. The target surface is generally composed of an inert material at a controlled temperature and serves to conduct heat to the particles for obtaining rapid solute vaporization. Once the solute is vaporized, Normal gas phase processes provide ionization such as electron impact or chemical ionization. A target surface with collected particles may be bombarded with ions, neutral, or electron beams to create gas-phase ions from the target surface. Alternatively, the solute is collected on a cold target surface for a period of time before heating the target, thus concentrating sample to lower the detection limits. Measurement of power supplied to the target can also be used to determine heat of vaporization.

The use of other gas-phase detectors such as the flame ionization detector (FID) require cryopumping for solute enrichment and hydrogen as the nebulization gas. This embodiment operates with atmospheric pressure or low pressure flames.

The particle beam embodiment is also used with laser scattering or continuum light scattering measurements and functions as a universal liquid chromatography detector.

The invention is illustrated in preferred embodiments in the accompanying drawings.

DETAILED DESCRIPTION OF THE PREFERRED EMBODIMENTS

The present device has three component parts: an aerosol generator 14, a solute enricher, and a solute collector or detector.

Figure 1:
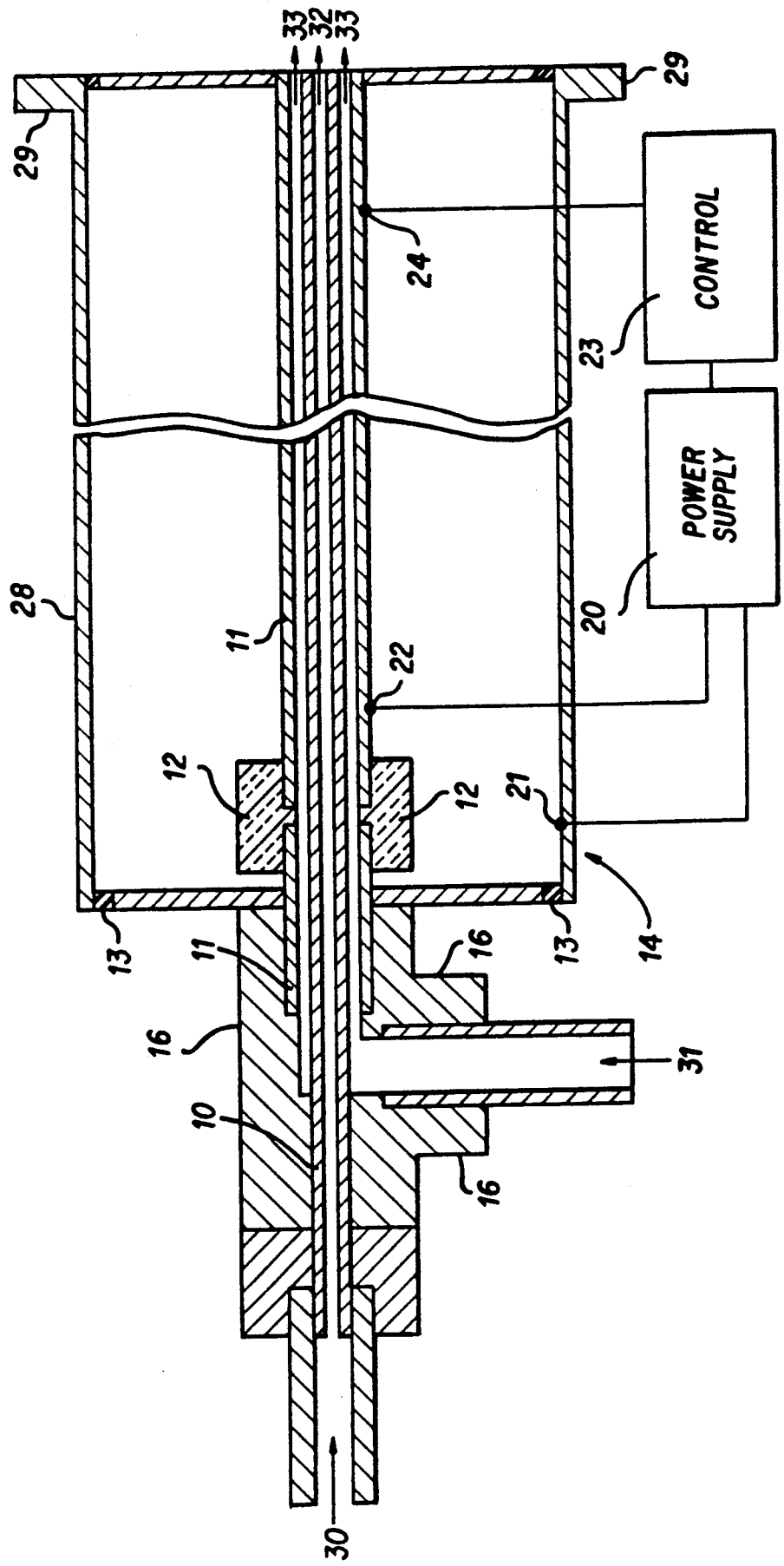
FIG. 1 is a schematic diagram in cross-section of a thermal concentric aerosol generating apparatus with resistive heating of the conductive aerosol generation gas.

The first of these component parts, aerosol generator 14, is described in detail with reference to FIGS. 1 and 2. Flowing into aerosol generator 14 is liquid from supply 30, and gas from supply 31. Gas flows through a conduit comprising a tube 11, and liquid through an inner capillary tube 10. Critical to the operation of aerosol generator 14 is the coaxial supply of heat across the flowing gas medium, between tubes 10 and 11, to flowing liquid in tube 10. The dimensions of the tubes and the flow rates of gas, liquid, and heat determine the properties of the generated aerosol.

The liquid supply 30 for the present aerosol generator is the effluent from liquid process streams, liquid chromatographs, or flow injection streams, the effluent containing dissolved analytes of interest in addition to other less volatile constituents, either present naturally or added purposefully. Fused silica capillary tube 10 function as a nozzle to confine the flow of the liquid effluent. Tube 10 restricts the flow of liquid resulting in increased linear velocity of the liquid stream as well as increased surface contact per unit volume of liquid with the heated walls of the fused silica capillary. The inner diameter of the fused silica capillary tube 10 has dimensions that are determined by the liquid flow requirements for a given application. The minimum inner diameter of tube 10 is determined by the upper pumping pressure limit of liquid supply 30. Liquid flow rate, length, and inner diameter of tube 10 have an effect the liquid supply pressure. Typical dimensions of the fused silica capillary for liquid flows in the range from 0.1 to 2.0 mL per minute is fifty micrometers inner diameter and two hundred and fifty micrometers outer diameter. Inner diameter dimensions for tube 10 have been successfully tested at ten micrometers, twenty-five micrometers, fifty micrometers, seventy-five micrometers, and one hundred micrometers. The length of the fused silica capillary tubing is that sufficient so that the heat transfer can vaporize the liquid stream before it leaves the tubing. A typical length is twenty centimeters. The maximum length of fused silica capillary tube 10 is determined by the pressure limit of the liquid pumping system.

Gas supply 31 for the aerosol generator 14 comprises a regulated gas source, compressed or self-generated, of a thermally conductive gas or mixture of gases. The coaxial metal capillary tube 11 sheathes the fused silica tube 10 and confines the flow of nebulizer gas supplied from a regulated gas supply 31 and controlled by precision valve 34 (seen in FIG. 3). The inner diameter of the metal capillary tube 11 and the gas flow rate from supply 31 determine the linear velocity of the gas through the metal capillary tube 32 and consequently, the linear velocity of the concentric sheath gas 33 in the aerosol generation process. The concentric gas flow serves two functions in the present device: First, to sheath the aerosol exiting the fused silica capillary tube 10. Second, to serve as a conductive medium for heat transport from the heated outer metal capillary tube 11 to the inner fused silica capillary tube 10.

The heat supply for the present aerosol generator is composed of electrical resistance of the metal capillary tube 11 which causes it to heat. FIG. 1 illustrates means for supplying heat to increase the temperature of capillary tube 11 by passing current through same; the tube being the resistively heated part of the heating circuit. The length, composition, and wall thickness of outer tube 11 determine the power requirements of the heating power supply 20, controlled by heater controller 23. The heating circuit is controlled by maintaining either constant resistance in the circuit or a constant temperature by means of thermocouple feedback 24. The heated outer tube 11 is preferably composed of a pure metal such as nickel or platinum because temperature is proportional to resistance for such pure metals as well as many other pure metals. This relationship permits control of the heat supply or temperature by direct resistance feedback measurement, without the requirement of thermocouple feedback control. The present device may also use thermocouple feedback for heat supply control and resistively heated alloys rather than pure metals. The resistively heating circuit is electrically isolated from ground by appropriate means such as insulators located at 12 and 13. The inner diameter of the heated metal capillary tube 11 is slightly larger than the outer diameter of the inner fused silica capillary tube 10. A typical range for the inner diameter of the tube 11 is three hundred to four hundred micrometers. In this range the gas velocity is sufficiently high to entrain the liquid jet or aerosol emerging from the fused silica capillary 10 at position 32. In addition, the interstitial spacing is small enough to allow efficient heat transport across the gas to the fused silica tube 10. There is a portion of capillary tube 11 that is not part of the resistively heated circuit and is connected to the heated portion of tube 11 by the electrically insulated union 12. The region surrounding the outer metal capillary tube 11 conducts heat at a slower rate compared to the rate of heat transport to the inner fused silica tube 10. Consequently, the outer tube is thermally insulated with an air space, a thermal insulating substance, or a vacuum, to ensure heat transport to the flowing liquid stream.

Figure 2:
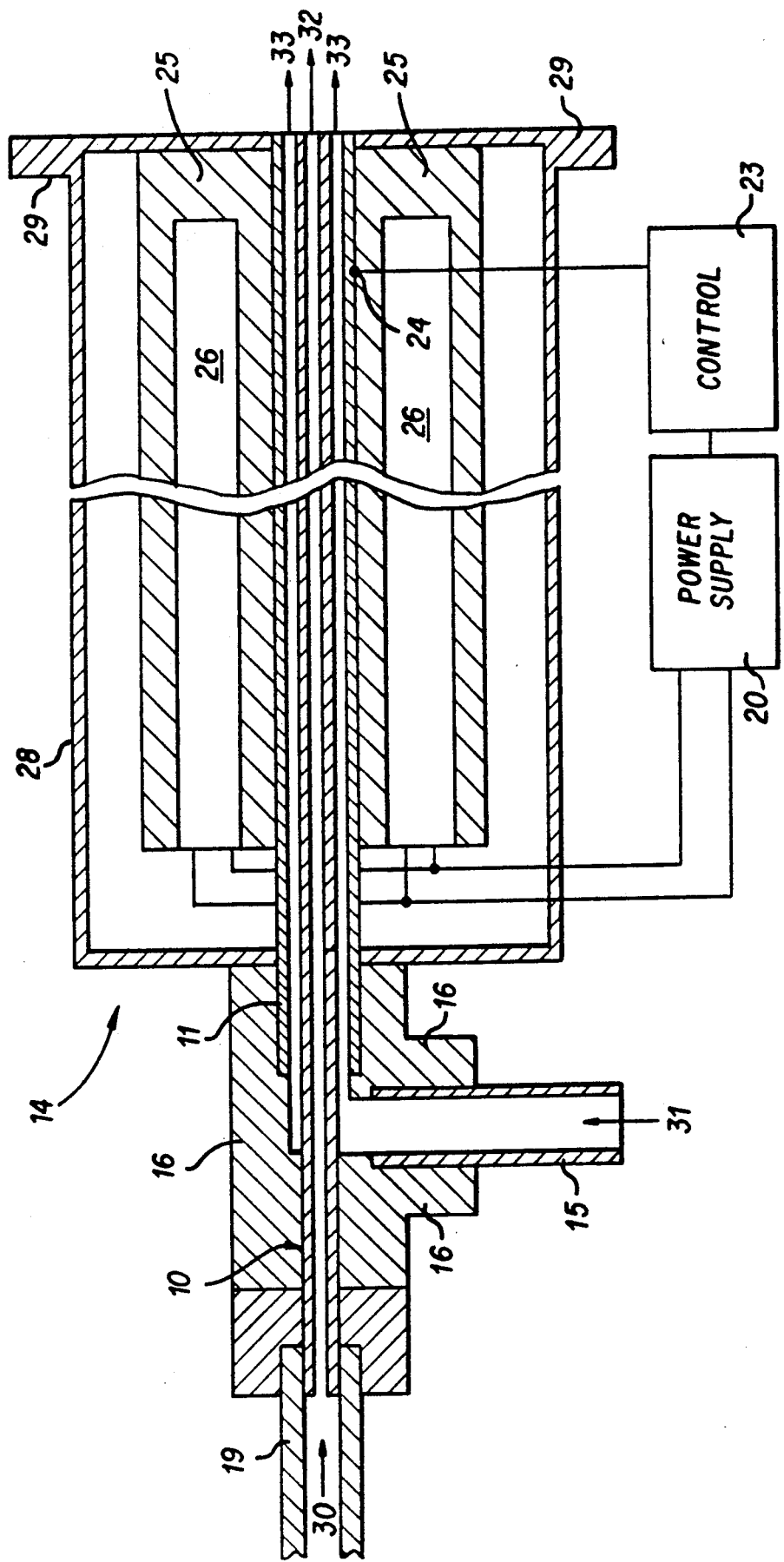
FIG. 2 is a schematic diagram in cross-section of a thermal concentric aerosol generating apparatus with cartridge heating of the conductive aerosol generation gas.

FIG. 2 illustrates an alternative means of heat supply to the metal capillary tube 11 by cartridge heating. Cartridge heaters 26 are inserted into a metal block in thermal contact with the metal capillary tube 11. With cartridge heaters, the means of control for the heater power supply 20 is through thermocouple feedback 24 to controller 23.

The heated portion of the aerosol generator is contained in a protective housing 28 that serves to support the aerosol generator as well as protect the operator from potential burns or electrical shock. The aerosol generator is attached to aerosol expansion chambers via connection 29 which may be a gasket or O-ring seal or both.

The aerosol generation with the present device is obtained by combining the coaxial flow of liquid, gas, and heat in a precisely controlled manner. The aerosol is generated at position 32 and confined along the axis in the direction of flow by sheath gas 33. The coaxial heat transport to the flowing liquid is controlled by electrical feedback circuitry and by the flow of gas between the outer heated metal tube 11 and the inner fused silica capillary tube 10, the gas being the conductive medium across the interstitial space. The thermal conductivity of the gas is a critical parameter in the transport of heat to the inner fused silica tube 10. It is preferred to have the gas supply constitute a high conductivity gas such as hydrogen or helium, but not excluding other less conductive gases or gas mixtures.

The preferred operation conditions for the present aerosol generator depend upon the required aerosol properties for a given application. The range of aerosol properties varies from a pneumaticly nebulized solvent-rich aerosol with relatively large diameter droplets to a thermally nebulized solvent-depleted aerosol with relatively small diameter droplets. The combined pneumatic and thermal nebulization processes yield aerosols that have controlled variation in droplet size, degree of desolvation of droplets, and direction of flow of the generated aerosol generator, as described, functioning to produce solvent-depleted solute particles.

Figure 3:
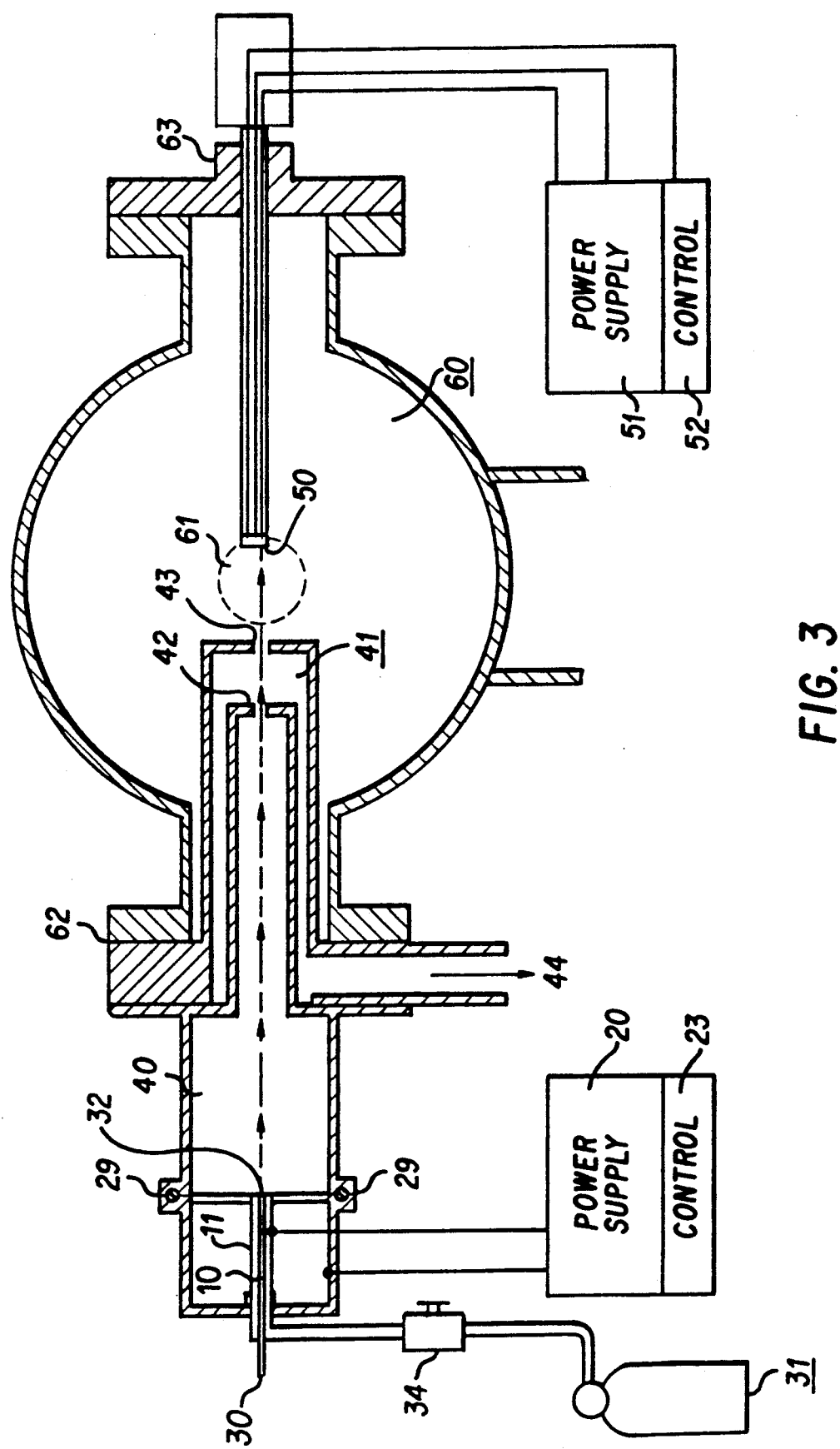
FIG. 3 is a schematic diagram in cross-section of a thermal concentric aerosol generating apparatus and single-stage particle beam solute enrichment to interface with a conventional mass spectrometer ion source chamber flange.
Figure 4:
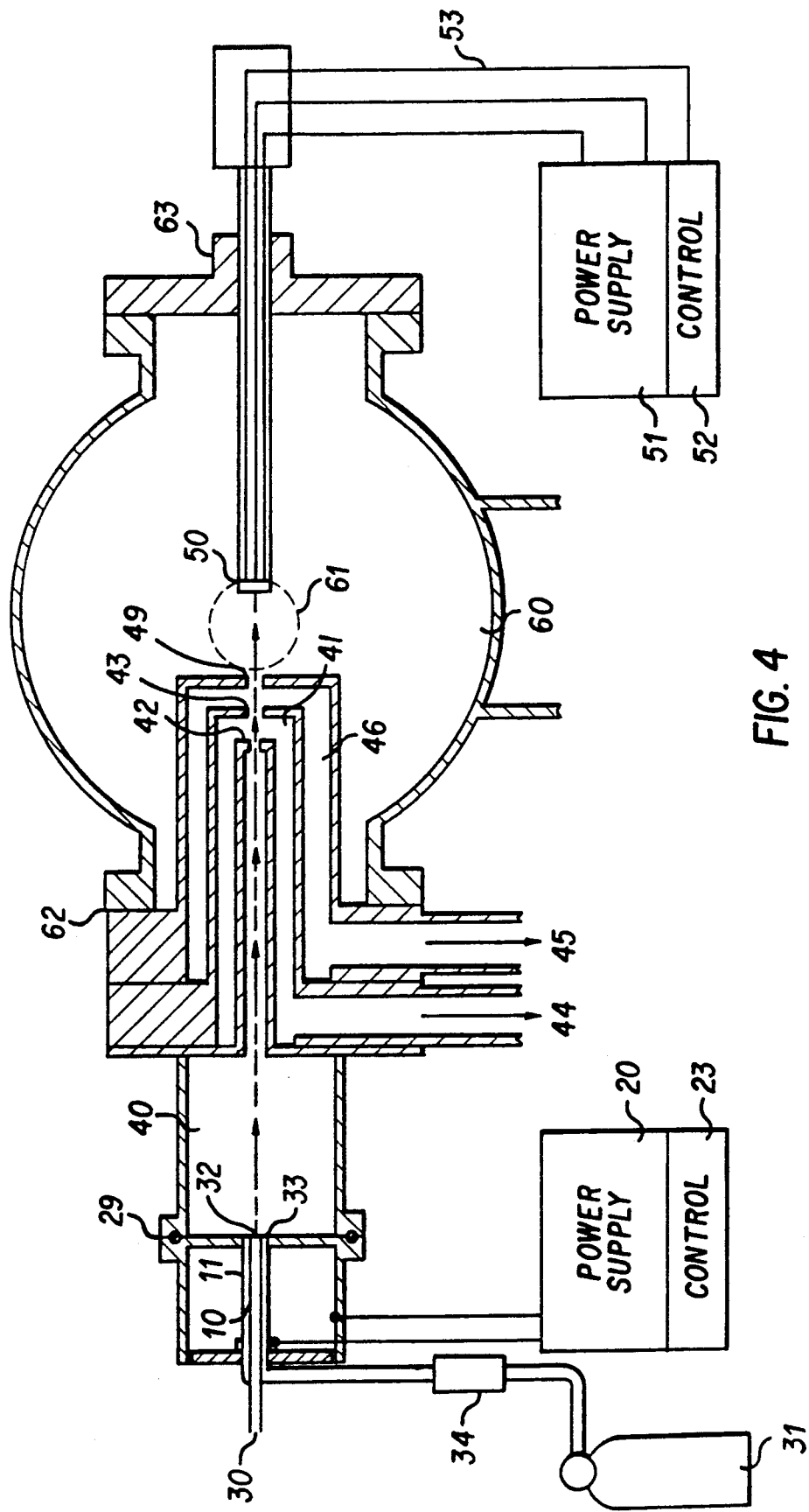
FIG. 4 is a schematic diagram in cross-section of a thermal concentric aerosol generating apparatus and dual-stage particle beam solution enrichment to interface with a conventional mass spectrometer ion source chamber flange.
Figure 5:
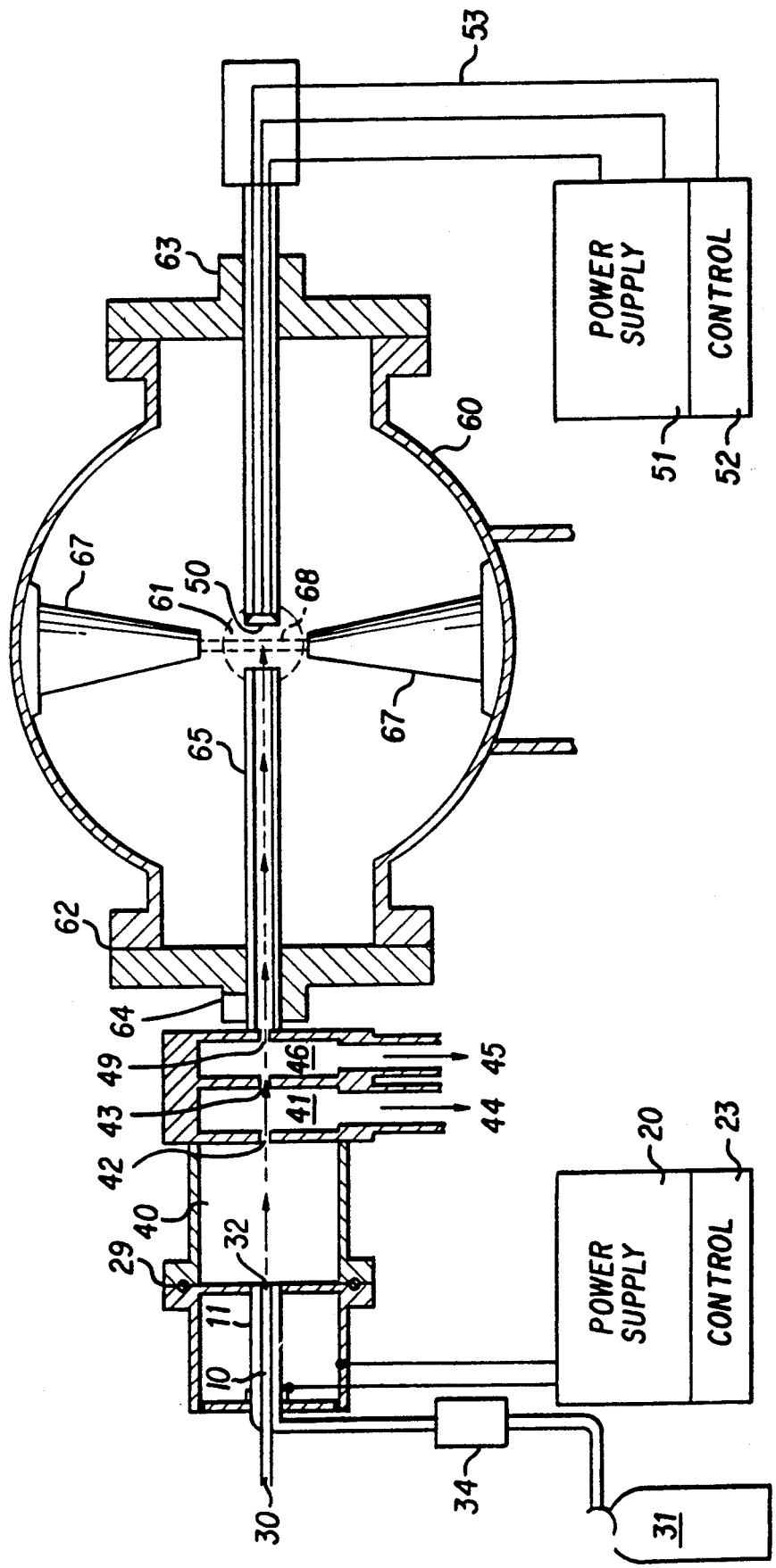
FIG. 5 is a schematic diagram in cross-section of a thermal concentric aerosol generating apparatus and an alternative embodiment of dual-stage particle beam solute enrichment to interface to a conventional mass spectrometer ion source chamber gate valve.
Figure 6:
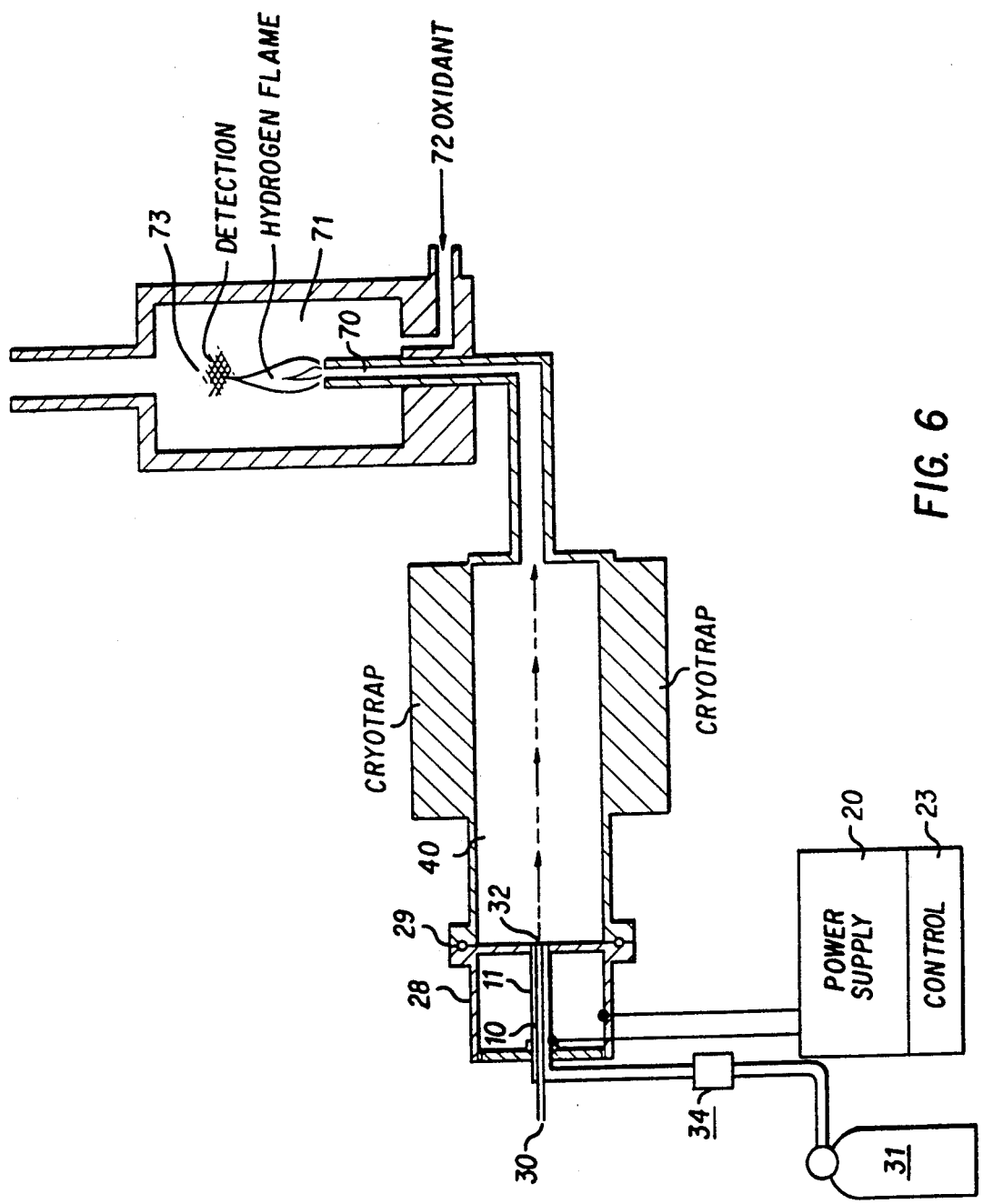
FIG. 6 is a diagrammatic view of a thermal concentric aerosol generating apparatus and solvent cryotrapping solute enrichment to interface to a flame ionization detector.

The aerosol generated with the present device requires a solute enrichment step in the embodiments where solute detection is degraded by the presence of proportionately large quantities of solvent. The present device is most generally applicable to effluents where the solutes are less volatile than the associated solvent or soluents. The volatility difference between the solvent and solute results in solute being predominately located in the particulate portion of the aerosol and the solvent predominately located in the vapor portion of the aerosol. FIGS. 3 through 5 illustrate embodiments of the present invention with aerosol generation, particle beam solute enrichment, and mass spectrometric detection. FIG. 6 illustrates an embodiment of the present device with aerosol generation, solvent cryotrapping for solute enrichment, and flame ionization detection. The application of the present device for aerosol generation, solute enrichment, and detection with other modes of detection are not illustrated, but the modifications necessary to attain same will occur to those knowledgeable in the field of liquid sample introduction into gas-phase or particulate detectors from the embodiments disclosed herein.

FIG. 3 depicts the embodiment of the present invention with single stage particle beam solute enrichment. The device is attached to an ion source chamber 60 of a mass spectrometer via a flange vacuum joint 62. The aerosol generator described previously is attached to an aerosol expansion chamber 40 by a sealed joint 29. Expansion chamber 40 provides sufficient space for the high velocity aerosol generated at 32 to be slowed in a viscous flow region and to proceed in the direction indicated by the dashed line and arrows. The pressure in the expansion chamber may vary from near atmospheric pressure down to a pressure adequate to reduce the velocity of the gas, solvent vapor and soluted particles entrained therein sufficiently so that those substances flow in a stream through the expansion chamber without significant loss of sample due to particle impaction on the inner surfaces of the expansion chamber or settling depending upon the mass flow rate from the aerosol generator. The solute particles, sheath gas, and solvent vapor are next accelerated through nozzle 42, forming a high velocity aerosol beam along a longitudinal axis between nozzle 42 and skimmer 43. The beam forms due to the pressure drop between expansion chamber 40 and vacuum chamber 41. Vacuum chamber 41 is evacuated by pump 44, generally a large pumping capacity mechanical pump such as a 400 l/min rotary pump. In the region between the axially aligned nozzle 42 and skimmer 43 the solvent vapor and conductive sheath gases from the aerosol expand significantly more rapidly than the solute particles. As a consequence of differential expansion of gases and particles, the particles are highly enriched at the axis of the expanding aerosol beam. The enriched solute particles are sampled into the ion source chamber of the mass spectrometer through skimmer 43. An enriched solute particle beam is formed from the skimmer to the ionization region of the mass spectrometer 61. The distance between the point where the aerosol beam is formed at nozzle 42 and the ionization region should be kept to a minimum, generally five to ten centimeters.

FIG. 4 illustrates the embodiment of the present invention with two-stage solute particle beam enrichment. As described with respect to FIG. 3, the device is attached to the ion source chamber 60 of a mass spectrometer via flange joint 62. The aerosol generator is attached to the aerosol expansion chamber 40 at sealed joint 29. The aerosol axially expands from the aerosol generator at 32 and proceeds down the axis of expansion chamber 40 in the direction indicated by the dashed line and arrows. The aerosol is accelerated through nozzle 42 forming a high velocity aerosol beam between nozzle 42 and skimmer 43. The aerosol beam is formed due to the pressure drop between the expansion chamber 40 and the first vacuum chamber 41. A second vacuum chamber 46 provides a higher degree of solute enrichment by pumping away additional solvent vapor in the region between skimmer 43 and skimmer 49. The first vacuum chamber 41 is evacuated by pump 44 and the second vacuum chamber is evacuated by pump 45. Pump 44 and 45 have sufficient pumping capability to remove most of the solvent vapor introduced by the aerosol generator. Nozzle 42 and skimmers 43 and 49 are, as before, axially aligned to permit sampling of enriched solute particles into progressively lower pressure regions. The distance between the nozzle 42, where the aerosol beam is formed, and the ionization region 61 is minimized to ensure solute particle transport efficiency. This distance is generally one to ten centimeters.

FIG. 5 illustrates an embodiment of the present invention with two-stage solute particle beam enrichment in an alternative embodiment to that shown in FIG. 4. The device is removable from the ion source chamber 60 of the mass spectrometer through a standard gate valve 64. The insertion probe portion 65 of this device is inserted into gate valve 64 (automatically opening same) so as to be axially aligned with the ionization region 61 of the mass spectrometer. The aerosol generator is attached to aerosol expansion chamber 40 at sealed joint 29. The aerosol axially expands from the aerosol generator at 32 and proceeds down the axis of the expansion chamber in the direction indicated by the dashed line and arrows. The aerosol is accelerated through nozzle 42 forming a high velocity aerosol beam between nozzle 42 and skimmer 43. The aerosol beam is formed due to the pressure drop between the expansion chamber 40 and the first vacuum chamber 41. A second vacuum chamber 46 provides a higher degree of solute enrichment by pumping away additional solvent vapor in the region between skimmer 43 and skimmer 49. First vacuum chamber 41 is evacuated by pump 44 and the second vacuum chamber is evacuated by pump 45. Pumps 44 and 45 have sufficient pumping capability to remove most of the solvent vapor and conductive gas introduced by the aerosol generator. Nozzle 42 and skimmers 43 and 49 are, as previously, axially aligned to permit sampling of enriched solute particles into progressively lower pressure regions. The distance between the nozzle 42, where the aerosol beam is formed, and the ionization region 61 is minimized to ensure solute particle transport efficiency; however, with this embodiment, the additional length of the intersection probe 65 is required. This distance is generally in a range of twenty to forty centimeters.

FIG. 5 also discloses optional attachments 67 which may be introduces into ion chamber 60 proximate to and around ionization region 61 for special purposes. For example, attachment 67 may be a laser whereby a laser beam is focused on to the surface of target 61, thus subjecting the beam to photoionization and laser desorption analysis. Also attachment 67 may constitute an electron source for chemical ionization or a high voltage source to ionize particles and molecules by discharge or field ionization.

Yet further, attachment 67 may comprise a cryotrap for collecting solvent vapor on cold surfaces while allowing solute particles to pass through the cold trap for subsequent detection. Another form of attachment 67 is apparatus for providing an optical region across the axis of the particle beam for making light scattering measurements on the beam. Attachment 67 may further comprise a support for a moving target, a belt 68 shown in dashes lines, which collects solute particles as a function of time, and wherein apparatus incorporated in attachment 67, or separate apparatus, subsequently locates and analyzes the chromatographic profile so received by surface measurement techniques such as SIMS, infra-red, x-ray, ultraviolet, or visible spectrophotometry scanning or the like such as reflectance or transmittance measurement techniques. Further, belt 68 may collect highly purified solute crystals for subsequent structure analysis. Belt 68 or its equivalent, such as disc or moving strip may be heated for a continuing on-line thermal analysis. In such event, attachment 67 also comprises means for heating the target, controlling such heat, and precisely measuring the thermal energy consumed by evaporation or desorption of solute from the target.

An attachment 67 can constitute apparatus for generating a high energy discharge of sufficient energy to charge surfaces of particles in the beam and thereby enhance ion desorption or particle fission by coulombic repulsion. Attachment 67 may be built-in or, preferably, readily attachable and removable, and plurality of attachments 67 may be disposed in chamber 60 operably proximate the target and region 61 and so that they may be employed alone or in combinations as desired.

The enriched particle beams produced with the embodiments shown in FIGS. 3 to 5 convert the solute particles into gas-phase ions in a similar manner. With each of these devices, the solute particles are collected on a target surface 50. The target surface 50 is a resistively heated surface that supplies thermal energy to minute solute particles to vaporize the solute molecules. The target is inserted through gate valve 63 so that solute vaporization occurs in the ionization region 61 of the mass spectrometer. The temperature of target surface 50 is controlled by controller 52 with thermocouple feedback 53 and power supply 51. The collected solute particles are heated at low temperatures for thermally sensitive compounds and at high temperatures for involatile species and atomization. The operating temperature range for target surface 50 range generally from one hundred degrees to three thousand degrees C. Ionization of the gas-phase solute molecules occurs by conventional ionization processes such as electron impact or chemical ionization.

The ionization processes occurring in the device described with respect to FIGS. 3-5 are not limited to gas-phase ionization. The solute particle beams are also collected on target surface 50 and ionized with conventional surface ionization techniques such as fast atom bombardment, secondary ion mass spectrometry, field desorption, thermal ionization, plasma desorption, and laser desorption as described with reference to FIG. 5. These techniques require the introduction of an alternative energy source to the target surface. In addition to surface ionization processes, the present device also permits the introduction of energy to the solute particle beam directly without collection of the particles on a surface prior to ionization. With this embodiment, target surface 50 need not be present. The solute particle beam intercepts, in flight, a primary ion beam, a primary atom beam, a laser beam, or a high field region.

FIG. 6 illustrates the embodiment of the present invention with solvent cryotrapping to provide solute particle enrichment. The aerosol generator is attached to the aerosol expansion chamber 40 at sealed joint 29. The conductive gas used for aerosol generation with this embodiment is hydrogen gas. The aerosol axially expands from the aerosol generator at 32 and proceeds down the axis of the expansion chamber in the direction indicated by the dashed line and arrows. The walls of the expansion chamber 40 are cryogenically cooled to trap the solvent vapor. The solute particles and hydrogen gas are passed through the expansion chamber more efficiently than the solvent vapor. The enriched solute particles and hydrogen gas are introduced into a burner chamber 71 through inlet 70. Here, the particles are burned in a hydrogen flame and the ions produced in the flame are collected on electrode grid 73. Air or oxygen is introduced into the burner chamber 71 through inlet 72.

The foregoing description of specific embodiments is for clearness of understanding by those skilled in the art and unnecessary limitations should not be unserstood therefrom. The cited prior art patents, literature and patent applications may assist in the understanding of the invention by those skilled in the art as well as those who may desire or need to acquire such an understanding.

Having disclosed by invention, what I claim as new and to be secure by Letters Patent of the United States is:

1. A method for generating and transporting highly dispersed aerosols from solutions containing low volatility solutes for sample introduction into detection devices, concentration of solute, or purification of solute, the method comprising the steps of:
   a. introducing a concentric flow of liquid and gas streams so that the gas flows outside the liquid flow,
   b. conducting heat to the inner liquid stream, via a highly conductive gaseous medium blanketing said liquid stream,
   c. nebulizing said liquid stream by,
      i. accelerating said liquid stream through a narrow tube to increase said stream's linear velocity and kinetic energy,
      ii. introducing into said liquid stream thermal energy across a conductive gas medium, and
      iii. introducing into said liquid stream mechanical energy from said conductive gas flow, so that the properties of the general aerosol can be changed by controlling the amount of each source of energy imparted to the liquid stream,
   d. controlling the supply of energy directed toward the aerosol generation process by,
      i. controlling the supply of heat to said conductive gas medium,
      ii. controlling the flow of conductive gas onto the outer flow region, and
      iii. controlling the flow rate of liquid into the nozzle of the aerosol generator, and
   e. removing the solvent vapor from the aerosol by cryogenic trapping of the vapor at about at least atmospheric pressure and passing dry solute particles for subsequent detection.

2. A method for thermally generating highly dispersed aerosols, which includes a separation step removing the solvent vapor from the aerosol by cryogenic trapping of the vapor at about at least atmospheric pressure and passing dry solute particles for subsequent detection.

3. A method for thermally generating a highly dispersed aerosol as defined in claim 2, which further includes an ionization detection of the particle stream.

4. A method for thermally generating a highly dispersed aerosol comprising solute particles, solvent vapor and dispersion gas wherein the motion of said particles is governed by viscous flow of the solvent vapor and dispersion gas as it moves towards a nozzle, which includes a separation step of removing solvent vapor and disperion gas from the aerosol by accelerating substantially all of the aerosol through said nozzle so that a high velocity collimated solute particle beam is formed after passing through said nozzle comprising substantially all of said solute particles that is axially aligned with the nozzle, and removing solvent vapor and dispersion gas from said particle beam by non-axial pumping.

5. A method for thermally generating a highly dispersed aerosol as defined in claim 4, which further includes a pressure reduction step of directing said high velocity solute particle beam through at least two skimmers which separate differentially pumped chambers.

6. A method for thermally generating a highly dispersed aerosol as defined in claim 4, which further includes a step of collecting the solvent-depleted solute particles from said aerosol on a target surface for subsequent analysis, the analysis selectively including:
   a. vaporization and ionization for mass spectrometric analysis, or
   b. x-ray diffraction analysis or other crystal or solid particle studying techniques, or
   c. optical analysis which includes infra-red reflectance or transmittance or other optical techniques using appropriate wavelengths, filters, or monochrometers.

7. A method for vaporizing the enriched solute particles by directing the particle beam in claim 5 onto a heated surface with sufficient surface area to collect said beam and a sufficient supply of thermal energy to evaporate the solute.

8. A method for vaporizing the enriched solute particles by directing the particle beam in claim 5 onto a heated surface with sufficient surface area to collect said beam and an alternative source of energy to cause evaporation, the alternative source of energy selectively comprising:
   a. a laser so that the solute molecules are desorbed from the collector surface using the process known as laser desorption, or
   b. by a beam so that solute molecules are desorbed from the collector surface using the process known as ion sputtering, or
   c. a high voltage field so that solute molecules are desorbed from the collector surface.

* * * * *